United States Patent [19]

Petersen et al.

[11] Patent Number: 4,939,574
[45] Date of Patent: Jul. 3, 1990

[54] METHOD AND APPARATUS FOR CLASSIFYING LIVESTOCK CARCASSES AND IN PARTICULAR CATTLE CARCASSES USING A DATA PROCESSING SYSTEM TO DETERMINE THE PROPERTIES OF THE CARCASS

[75] Inventors: Freddy Petersen, Jyllinge; Svend E. Soerensen, Albertslund; Signe Klastrup, Valby, all of Denmark

[73] Assignee: Slagteriernes Forskningsinstitut, Roskilde, Denmark

[21] Appl. No.: 287,117

[22] Filed: Dec. 21, 1988

[30] Foreign Application Priority Data

Dec. 22, 1987 [DK] Denmark .............................. 6764/87

[51] Int. Cl.⁵ .............................................. H04N 7/18
[52] U.S. Cl. ....................................... 358/93; 358/107; 356/445
[58] Field of Search .................. 352/121, 106, 107, 93, 352/96; 73/104, 105; 356/445, 237; 382/6, 8; 426/231

[56] References Cited

U.S. PATENT DOCUMENTS

| | | | |
|---|---|---|---|
| 4,226,540 | 10/1980 | Barten et al. | 356/445 |
| 4,413,279 | 11/1983 | Görl | 358/107 |
| 4,439,037 | 3/1984 | Northeved et al. | 356/445 X |
| 4,745,472 | 5/1988 | Hayes | 358/107 |

Primary Examiner—James J. Groody
Assistant Examiner—Victor R. Kostak
Attorney, Agent, or Firm—Fleit, Jacobson, Cohn, Price, Holman & Stern

[57] ABSTRACT

For determining properties of individual livestock carcass, in particular cattle carcasses, a carcass or half of a split carcass is placed in a light-screening chamber in front of a light-emitting, contrasting surface. The carcass stands out as a dark silhouette against the contrasting surface and a picture of one entire side of the carcass is registered by means of a video camera. The contour of the carcass is determined by processing the registered picture in a data processing system, and on the basis of the contour determined in the processing system, a calculation of the parameters is performed in the data processing system for determining the properties of the carcass, the result of the determination being displayed or printed out.

15 Claims, 3 Drawing Sheets

METHOD AND APPARATUS FOR CLASSIFYING LIVESTOCK CARCASSES AND IN PARTICULAR CATTLE CARCASSES USING A DATA PROCESSING SYSTEM TO DETERMINE THE PROPERTIES OF THE CARCASS

TITLE OF THE INVENTION

The present invention relates to a method and apparatus for the determination of quality properties of individual cattle carcasses.

BACKGROUND OF THE INVENTION

At slaughterhouses a classification of the individual cattle carcasses is made in order to establish a price between the farmer and the slaughterhouse which is in accordance with the quality of the carcasses. A skilled classification expert appraises the conformation and fat cover of the individual carcasses and fixes their category. The expert then grades the carcasses in accordance with a classification system.

The system applied within the EEC comprises five classes of conformation designated E, U, R, O and P. In order to be given an E classification the carcass must have an excellent conformation and be without defects in respect of its essential parts. All profiles must be convex to super-convex, and the muscles must be exceptionally developed. The round must be very rounded, and the back wide and very thick, up to the shoulder which must be very rounded.

The grades U, R, O, and P are awarded less valuable carcasses. Thus, the grade P (poor) is given for carcasses with profiles which are concave to very concave and with muscles which are poorly developed. In these carcasses the round is poorly developed, the back is narrow with visible bones, and the shoulder is flat with visible bones.

In order to achieve a higher differentiation in the fixing of the price each class may be divided into three sub-classes. Thus, the grade E− denotes a carcass graded in the lower third of the class E, whereas the grade E+ denotes a carcass in the top third.

The system includes five classes of fatness, 1 to 5. Grade 1 is given for carcasses without or with a low fat cover, and without fat within the thoracic cavity. Grade 5 means that the entire carcass is covered with fat and that there are heavy deposits of fat in the thoracic cavity. The round is almost completely covered with fat, so that the seams of fat are no longer clearly visible. In the thoracic cavity the muscle between the ribs is infiltrated with fat.

Cattle carcasses which represent the extreme grades of the scales can fairly easily be distinguished from each other. On the other hand, great experience is required to make a sure classfication of carcasses which differ from each other by one step on the scale. This is particularly true for carcasses which are graded in the intermediate classes, where good and poor properties are present in a mixture, and these must be weighed against each other. Unfortunately, the situation is that the majority of the carcasses occur in the intermediate classes. This means that the classification may be uncertain, with a risk that the prices are fixed on a wrong level.

Another thing is that the class only to a certain extent reflects the value of the carcasses. The classification must be considered as a rough division of the carcasses into various groups only, which may each, by experience, represent a price category. The same class may quite well include carcasses with different composition as regards lean, fat and bone, and consequently with different prices per kg.

The exact value of the individual carcass can only be fixed by dissection of the carcass and assessing the individual cuts. A substantial effort of work and assessment is required, which is not possible for practical reasons. Among the qualities which influence the value of the carcass may be mentioned: the yield of saleable meat, distribution of meat of the carcass, the content of fat of the carcass, muscular volume, colour of the meat, colour of the fat, marbling, tenderness and taste.

A need exists for a semi or fully automatic method which may replace the above mentioned subjective classification procedure by a sure, objective classification of cattle carcasses. If possible, the method should also provide information about other properties of the individual carcasses which affect the value of the carcasses.

In a publication is described an attempt to provide an objective classification of cattle carcasses by means of video recording. (S. E. Sorensen: "Possibilities for Application of Video Image Analysis in Beef Carcass Classification" in In vivo measurement of body composition in meat animals, Elsevier (1984), p. 113–122). The carcass is positioned in front of a video camera on a dark background and a video picture is registered and the gray values stored in a memory. By processing the values in a computer system the boundary of the carcass is determined. Different parameters, such as width of the breast, waist, thigh and carcass area may be calculated on the basis of the boundary, and it is suggested that the conformation and lean/bone ratio may be estimated if the parameters are used in a formula obtained by regression analysis.

Likewise, the gray value distribution within the carcass boundary may be calculated and it is suggested to estimate a class of fatness by using the result in a formula obtained by regression analysis.

In the publication it is mentioned that the application of video image analysis for carcass grading is far from simple and several potential problems are to be considered. It is concluded that a thorough optimization of the analysis procedures is required and for optimal performance the method might have to include the third dimension.

It is known to classify pig carcasses by means of weight of the carcass and some measures of meat thickness and fat thickness. They are converted into a meat-percentage which is used for the fixing of the price. The thicknesses are measured by means of an instrument with a probe which an operator inserts at certain places of the carcass.

Furthermore, it is known to measure the meat and fat percentage of cattle carcasses by means of said instrument. However, an objective classification of cattle in accordance with the systems valid today cannot be performed in this way, as there does not exist any usable correlation between such measurements of thickness and classes.

In the patent literature various methods have been suggested to provide results of measurements which can reflect quality properties in individual pig or cattle carcasses and which may be used as a basis for an objective classification.

French Patent No. 2,546,423 describes an apparatus designed for automatic measuring classification parameters of cattle carcasses. The apparatus comprises an arrangement with a frame having a supporting surface for a split cattle carcass. A complicated mechanical system with mechanical sensors measures the essential dimensions of the carcass. This apparatus requires a high degree of maintenance of the mechnical parts, and the veterinary authorities may demand a sterilisation of every sensor between each measurement. The apparatus is not capable of determining the class of fatness or the composition of cattle carcasses.

West German Patent No. 27 28 913 describes an apparatus for the classification of pig carcasses in accordance with the system used in West Germany.

The apparatus comprises a dark chamber provided with a colour video camera and some daylight sources. A split pig carcass is placed in the chamber in such a way that the cut surface is facing the camera and the light sources. Parameters of the cut surface, such as the meat and fat thicknesses are determined by means of the camera and processed in a micro processor system. The camera registers the wall of the chamber as black, the fat as white and the meat as red. In this way the camera differentiates the different materials.

Based upon the recording and the weight of the carcass the class of quality may be calculated in the computer of the apparatus, and a mark denoting the class is automatically applied to the carcass by means of a stamping device.

French Patent No. 2,545,010 also describes an apparatus for the classification of pig carcasses. In this apparatus the height of an ultrasonic probe is set by means of a video recording of the cut surface of a split carcass. Furthermore, the recording of the camera is used for the determination of thicknesses in the cut surface. These thicknesses and the ones determined by the ultrasonic probe are used in the calculation determining the class of the pig carcass.

Thus, the literature has proposed different methods in which a video recording is used in the semi or fully automatic classification of carcasses, but no one has provided a method for the classification of cattle carcasses which is sufficiently accurate in practice to determine the composition and the conformation class as well as the class of fatness in an objective way. Such a method would be very difficult to provide in comparison with the current objective classification of pig carcasses in which it is sufficient to determine a few thicknesses of meat and fat. Even within the same category cattle carcasses may be very heterogeneous.

Furthermore, the thicknesses of meat and fat may not always be determined by means of a video recording of the cut surface of the carcass because some slaughterhouses do not split carcasses until after the classification procedure.

SUMMARY OF THE INVENTION

The object of the present invention is to provide a method and an apparatus wherein quality properties of significance for the value of the individual cattle carcasses may be determined in an accurate way by means of a video system. Preferably, an accurate, objective determination of the carcass composition and the conformation and fatness classes approved by the authorities should be provided.

The method of the invention comprises the step of:
placing a carcass or half of a split carcass in a light-screening chamber in front of a light emitting, contrasting surface,
while the carcass stands out as a dark silhouette against the contrasting surface, registering a picture of one entire side of the carcass with an electronic camera facing the contrasting surface,
determining the contour of the carcass by processing the registered picture by means of a data processing system,
on the basis of the determined contour, performing a calculation of parameters in the data processing system to determine the quality properties of the individual carcass, and
outputting the determined quality properties of the carcass.

The method of this invention provides a very accurate picture of the contour of the individual carcasses, because the side facing the camera is without illumination and the background appears as a lighting surface. A very sharp contrast in the picture between carcass and background is provided, and reflections originating from the reflection of the front illumination on the surface of the carcass are avoided.

The method of the invention has made it possible to determine the composition and classes of conformation and fatness of the individual cattle carcasses in an accurate and objective way during production conditions on the slaughter line. By means of the method the class of conformation and fatness has been determined with sufficient accuracy to replace the subjective classification used today.

Other quality properties of importance for the value of the individual carcasses, such as distribution of meat, may also be determined on the basis of the contour of the individual carcass. A more accurate price fixing than before may be made, based on these data, and the carcasses may be used in better accordance with their proper qualities.

The contour of the carcass is determined by processing the recorded picture in a processing system. By performing calculations, information of the size and dimensions of the carcass may then be provided. The parameters may be related to the classes of conformation. The parameters may e.g. be inserted in a formula provided in the computer system which reflects the conformation class on the basis of some variables of the contour picture.

According to an embodiment one or more dimensions of the carcass are determined on the basis of the registered contour and recognizable points therein. This reduces the extent of the data processing which is necessary for the determination of the conformation class. The dimensions obtained may be inserted in an algorithm which determines the conformation class of the carcass.

The rump and neck of the carcass may fairly easily be determined by analyzing the contour, and by means of these two fixed points the width of the carcass may be determined halfway between the points and at other places wanted.

The contour obtained according to the method of the invention may also be used to establish a border line in a video recording of the carcass made with frontal illumination. In this way a very accurate border line between the carcass and the background is drawn and irrelevant picture contents and sources of error may be removed before the content of the picture is analyzed, e.g. before the fat areas are determined. A correlation exists between the class of fatness and the percentage of the fat cover.

By inserting a probe instrument into the carcass the video measurement may be supplemented and further information of the carcass in question may be obtained, e.g. a more precise information of the composition, the yield to be expected and the muscular volume. The probe instrument may measure thicknesses of fat and meat, and these data together with the information from the picture recording may give a fairly precise indication of the quality properties of the carcass.

In accordance with this a second embodiment comprises registration of the thicknesses of meat and fat at selected places by inserting a probe into the carcass, and application of the measurements as parameters in the data processing system to determine quality properties.

The probe instrument may have a probe provided with a light emitter and a light receiver near the point of the probe. Such an instrument based upon reflection of light, is fairly precise in determining the thicknesses.

In order to improve the accuracy, measuring of thicknesses may be made at anatomically identical places on the right and the left half of the carcass, so that the accuracy of the measurement may be increased by calculating the average thicknesses and/or by detecting unacceptable deviations.

As mentioned above the contour may be used to establish a border line in a recording with facial illumination. In a special embodiment it is possible to provide a registration of a picture of the individual carcasses wherein the individual points of the picture may be differentiated from the background with a good accuracy and wherein the values of the points reflect, with good certainty, whether the surface of the carcass at the points in question consists of meat or fat. Consequently, the values may form the basis of an objective determination of the class of fatness. The embodiment comprises a method wherein a second picture of the carcass is registered by means of the electronic camera with illumination on the side of the carcass facing the camera and the registered picture and determined contour are processed in the data processing system to mask the background of this second picture and to discriminate between meat and fat areas on the carcass surface; the resulting areas are used as parameters in the data processing system to determine the quality properties of the carcass.

An optical distinction between areas of meat and fat on the surface of cattle carcasses may be difficult to perform for natural reasons, such as discolouration of the fat, membranes on the meat, reflections of light on the surface and instability in the illumination and camera sensitivity under slaughterhouse conditions.

It is possible to reduce these disturbances to a level where they influence to a minor degree the determination of the class of the individual carcasses. The reduction is obtained in that a partial picture of the registered picture is defined by means of the determined contour of the individual carcass and the light reflection values for the picture elements of this partial picture are processed statistically to discriminate between meat and fat areas.

In this embodiment it is of importance for the accuracy that a partial picture is defined and that the light reflection values in this are processed statistically in order to provide a threshold value between meat and fat. Light reflection values above the threshold value may represent areas of fat. The number of such values reflects the area of the fat cover of the carcass in question. Together with the other parameters measured, the area of the fat cover may be inserted in an algorithm which refers the carcass to one of the five classes of fatness.

The carcass may appropriately be illuminated with several sources of light, as this will reduce the effect of shadows and result in a more homogeneous illumination on the surface of the carcass.

In a preferred embodiment the side of the carcass facing the camera is illuminated by light of a diffuse character during the registration of the said second picture. This gives a highly homogeneous illumination of the surface of the carcass, free from any effects of shadows caused by the structure of the surface. Moreover, reflections from lamps and the like on the surface are prevented. In this embodiment the individual, measured light reflection values from the carcass represent a nearly true picture of the reflective power of the surface of the carcass.

A colour camera may be used for the recording in question, as this may distinguish the red areas of meat from the white to yellow areas of tallow.

Because of the statistical data processing of the light reflection values, however, a black/white camera is primarily used for the recording. Then, the light reflection value of each picture element in the recording is only represented by one number. In order to register the reflection values with sufficient accuracy, a tone-of-grey scale with a certain number of steps may be applied. It is appropriate to use a scale with e.g. 256 steps.

Even with a high number of tone-of-grey steps it may be difficult to distinguish the areas of meat and the areas of fat on the registered black/white picture from each other. The illumination used for the recording is primarily of a type which produces a greater difference in the reflective power of meat and fat than does illumination with white light. Ultraviolet light may for instance be used, which gives different fluorescence in surfaces of meat and fat.

Illumination with green light is primarily used, as this is extinguished on red surfaces, such as meat, whereas it is reflected very well from white or whitish surfaces, such as fat.

The light emitting contrasting surface used by the method of this invention may be a surface of frosted glass, which is illuminated from the back. According to the method of the invention the carcass is without illumination on the side facing the camera while the first recording is being performed. The carcass will stand out as a black silhouette against a light background, which is the frosted glass plate. This silhouette forms the contour which may be used to determine the class of conformation. In the embodiment with two recordings it also defines the area where the fat cover is to be looked for in the second recording, and in this it may serve as a mask for the second recording. This recording may be demasked in a computer programme by means of the first recording, so that it will only include reflection values from the carcass itself.

In order to obtain representative figures of the class of fatness of the individual carcass, a partial picture within the recording of the side of the carcass may be defined. The border line of the partial picture may depend on the dimension of the individual carcass. Easily recognizable points may be used to determine the border line of the partial picture.

In an embodiment a partial picture is used, the lower border line of which is the horizontal line which intersects the top point of the contour curve along the neck and the front legs of the carcass.

The recording may also be cut off above the horizontal line through the hind legs of the carcass which has a predetermined length in the recording, e.g. ten picture elements.

The light reflection values of each picture element in the defined partial picture represent an area of meat or fat, dependent on the criterion used in the statistical processing of the data. As criterion is primarily used a threshold value obtained by data processing of the light reflection values. The threshold value divides the data up into two groups. Registered light reflection values which are below the threshold value fall into the group which gives a measure for the meat area of the carcass. Reflection values above the threshold value belong to the other group, which gives a measure for the area of fat.

The threshold value is primarily determined on the basis of the frequency of the picture elements at the different reflection values.

A discriminative analysis may be made on these frequencies to determine the threshold value. The threshold value is primarily calculated as the light reflection value at which the variance of the frequency of the picture elements is at a maximum. This gives the best possible separation between two groups which are overlapping each other.

On the basis of the relative or absolute sizes of the fat cover on the individual carcasses, calculated in this way and preferably also on the basis of the fat thickness measured by means of the above mentioned probe instrument, the class of fatness of the individual carcass may be determined.

Within the areas of fat the colour class of the carcass (fat colour)—if desired—may be determined by the average colour being measured.

The method of the invention may comprise the following steps:
  placing a carcass or half of a split carcass in a light-screening chamber in front of a light-emitting, contrasting surface,
  while the carcass stands out as a dark silhouette against the contrasting surface, registering a first picture of one entire side of the carcass with an electronic camera facing the contrasting surface,
  illuminating one side of the carcass facing the camera,
  while said side is illuminated, registering a second picture of the side of the carcass with the electronic camera,
  determining the contour of the carcass by processing the registered first picture by means of a data processing system,
  defining a partial picture of the registered second picture by means of the determined contour and processing the light reflection values for the elements of said partial picture to discriminate between meat and fat areas,
  if desired, measuring the thicknesses of meat and fat at selected places on the carcass by inserting a probe into the carcass,
  on the basis of the determined contour, areas and thicknesses performing a calculation of the parameters in the data processing system to determine the relevant quality properties of the individual carcass, and
  outputting the determined properties of the carcass.

In the calculation of the composition, the classes of conformation and fatness and other quality properties, such as yield, use may also be made of available data of the individual carcass, such as weight.

The apparatus of this invention comprises:
  a light-screening chamber having a light-emitting, contrasting surface and means for placing a carcass or half of a split carcass in front of said contrasting surface,
  an electronic camera facing the contrasting surface to register a picture of one entire side of the carcass while it stands out as a dark silhouette against the contrasting surface,
  a data processing system designed to determine the contour of the carcass by processing the registered picture, said system on the basis of the determined contour performing a calculation of parameters to determine the quality properties of the individual carcass, and
  a data channel for outputting the determined quality properties of the carcass.

The light-emitting contrasting surface may be of an essentially homogeneous surface brightness. The apparatus may comprise an instrument with a probe for insertion into a carcass to register the thicknesses of meat and fat.

Furthermore, the apparatus may comprise an arrangement for the illumination on the side of the carcass facing the camera, and a programme in the data processing system to demask the background of the second picture and to discriminate between meat and fat areas of a registered picture.

The apparatus may be designed to generate light of a diffuse character. It may include a frosted, translucent plate, behind which several sources of light are placed.

The information obtained by the method of the invention may, in addition to the above mentioned determination of quality properties be used for automatic control of a transportation and treatment system, e.g. for automatic sorting of the carcass and their parts.

The method and the apparatus according to the invention may be applied to the classification of different categories of cattle. The word cattle in the present description is to be understood as calves, steers, young bulls, bulls, heifers and cows as well as sheep (lamb and adult sheep).

BRIEF DESCRIPTION OF THE DRAWINGS

The invention is described in further detail below, with reference to the drawings, wherein.

DESCRIPTION OF THE PREFERRED EMBODIMENTS

Figure 1:
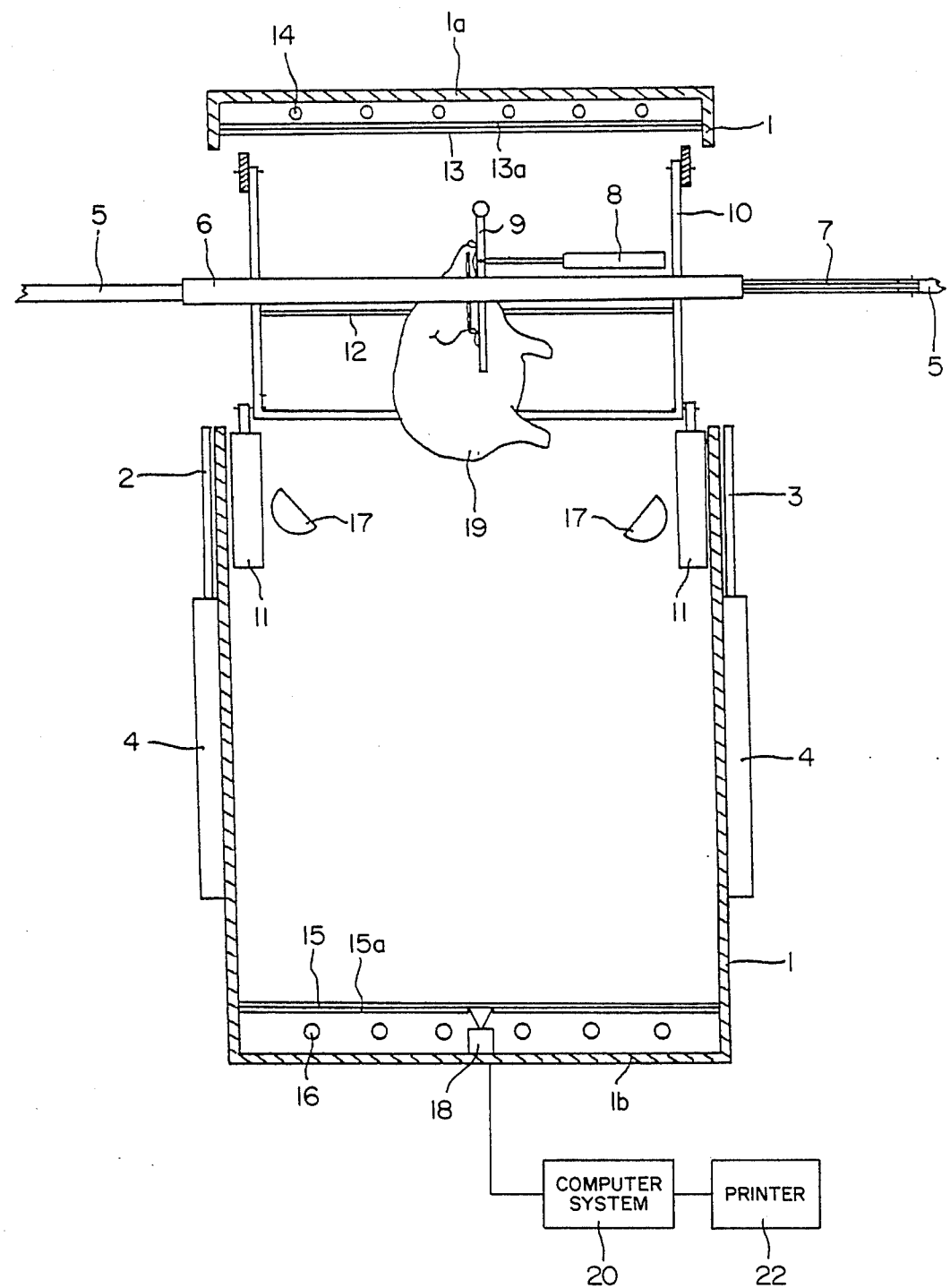
FIG. 1 is a top view of an apparatus for the classification of cattle carcasses with a positioned carcass.

The apparatus comprises a chamber 1 made of stainless steel. Two doors 2 and 3 in the chamber may be opened and closed by means of pneumatic cylinder units 4. A rail 5 is passing through the chamber. A carcass 19 suspended from a hook device may be conveyed along this rail. Parallel to the rail in the chamber is a pneumatic cylinder unit 6 equipped with a driving device 7 (FIG. 2) designed to pull the hook device and the suspended carcass to the area of registration in the centre of the chamber. Located here is a pivoting arm 9, operated by a cylinder unit 8, at the level of the hind legs of the carcass. When the cylinder unit 8 is activated, the arm 9 pushes the carcass along the rail until the arm reaches its end position, in which the carcass assumes a correct position for registration in the centre of the chamber. The arm 9 positions the entire carcass with the one side facing the camera, when the two hind legs of the carcass lie true against the arm 9 at the end position (FIG. 1).

At a following stroke of the cylinder unit 6 the driving device 7 is designed to pull the hook device and the carcass out of the chamber and along the rail 5, until they are again conveyed by the chain conveyor system of the slaughter line or by other conveyor systems.

A frame 10 is suspended from the roof of the chamber in such a way that it may swing to an active position when it is actuated by the piston rods of two cylinder units 11, which are located at the bottom of the chamber. By the actuation the lower part of the frame is moved away from the wall 1a of the chamber. Located approx. in the middle of the frame is a thin, horizontal rod 12 which is fastened to the vertical sides of the frame.

Located in front of the wall 1a is a frosted glass plate 13 with the frosted side away from the wall in order to reduce light reflections. Substantially, the glass plate covers the entire height and width of the chamber. Placed immediately behind the glass plate 13 is a diffuser in the form of a milky white acrylic plate 13a. Between this plate and the wall 1a of the chamber is placed a number of fluorescent tubes 14, which are so close to each other that a uniform surface brightness of the glass plate 13 is obtained. When the tubes are switched on the glass plate in the chamber will appear as a homogenously milky-white surface of light.

Located in front of the opposite wall 1b of the chamber are a corresponding frosted glass plate 15 and an acrylic plate 15a, which essentially cover the entire height and width of the chamber. Between the glass plate and the wall 1b is placed a number of green fluorescent tubes 16, which are so close to each other that the glass plate appears as an essentially homogeneous surface of light when the tubes are on.

Near each of the doors 2 and 3 are mounted a lamp 17 including a reflector, two green, vertically positioned fluorescent tubes, and a diffusor. The lamps are directed towards the area in the chamber, where a carcass is shown.

A video camera 18 of the type CCD is located in an opening cut out in the middle of the wall 1b. The camera is directed towards the opposite wall 1a of the chamber, so that a recording may be made of a carcass 19 (FIG. 1). The visual field of the camera is restricted by means of a mask.

The camera is linked up with a computer system 20 which includes a picture registration unit and a data processing unit. In the system are also a control unit for the mechanical components of the apparatus including the operating cylinder units, and a programme which takes care that the actions take place at the right time and in the right order.

Connected with the computer system are external units for the registration of further data of the individual carcasses, e.g. a keyboard terminal for manual input of slaughtering identification and codes, a weight arrangement for registration of the weight of the carcass, and a probe instrument for the registration of thicknesses of meat and fat at one or more places on the carcass.

The registration of quality properties of a carcass may be made in the following way in the apparatus described:

A carcass is conveyed to the door 2 by the conveyor system of the slaughter line and is then pulled along the rail 5 to approx. the centre of the chamber 1 by means of the driving device 7 and the cylinder unit 6. The doors 2 and 3 are closed by means of the cylinder units 4.

The cylinder unit 8 is actuated, so that the arm 9 conveys the hook device and the carcass 19 to the exact position at the centre of the chamber as shown. Then the cylinder units 11 are actuated, so that the lower part of the frame 10 swings somewhat away from the wall 1a. This brings the carcass in contact with the rod 12. In the resulting position of rest one side of the carcass faces the camera 18.

By means of the camera 18 a recording of the side of the carcass is performed while the background light from the fluorescent tubes 14 is switched on. Next, the front light is switched on, consisting of the fluorescent tubes 16 and the lamps 17, and a second recording is made of the side of the carcass by means of the camera. The background light is also switched on during this second recording. The recordings are transmitted electronically to the computer system, in which they are immediately processed as described below.

After the second recording the tubes 16 and the lamps 17 are switched off. The doors 2 and 3 are opened by means of the cylinder units 4. The cylinder unit 8 swings back the arm 9 to a position of release of the carcass, in which the driving device 7 and the cylinder unit 6 pulls the hook device and carcass out of the chamber along the rail 5.

When the carcass is outside the chamber an operator keyes the slaughtering number and class of colour into the computer system. The operator also measures the thicknesses of meat and fat by means of a probe instrument which he inserts at several places on the carcass. Afterwards, the carcass is given over to the ordinary conveyor system of the slaughter line for further treatment.

The first recording is processed in the computer system. A programme is defining the contour curve of the carcass on the basis of a substantial increment in the registered values of reflection occuring on the border line between the carcass and the background.

The contour curve forms the basis for the calculation of the carcass composition and the class of conformation in the computer. The convexity of the leg is calculated for instance by means of the lengths of three horizontal lines which connect points on the contour of the back of the leg and a vertical line of reference. When the length of the line in the middle is proportionally longer than the two other lengths, the shape of the leg is convex.

The contour curve also defines the area in which the carcass exists and is used for demasking the second recording stored in the computer system.

This area is limited at the top and at the bottom by means of data processing. At the top the border line is at the Y-co-ordinate where the sum of the number of picture elements inside the curve in the X-co-ordinate direction for the first time is 10 or more, when moving from high Y-values towards lower Y-values.

At the bottom the border line is at the Y-co-ordinate where a horizontal line only intersects the curve in two points when moving from low Y-values towards increasing Y-values at the area of the neck.

The closed curve, which is procured in this way by processing of the first recording, defines the area within which meat and fat is to be registered in the second recording with front illumination.

At the processing of the picture elements of the second recording, a masking is being made of the picture elements which fall outside the area which is determined by the first recording and the abovementioned processing. The masking is effected by a programme in the computer system.

Accordingly, there is a set of numbers stored in the memory of the system, each number representing a reflection value for a point on the outer surface of the carcass which can be registered by the camera. A high value is equal to an area of fat, whereas a low value represents meat. A medium value may for some recordings mean meat, and in other cases fat, dependent on natural variations, such as ageing or contamination of the light source, colour of the fat, heterogeneous conditions of reflection, etc. The set of numbers stored is subjected to a processing which in a more accurate way than with a fixed threshold value defines which numbers represent meat and which numbers represent fat.

The processing of the set of numbers is effected primarily by expressing it in a histogram with tone-of-grey values as a basis, and the frequency as a function of this. The histogram may be normalized. The variance of several tone-of-grey values in the tone-of-grey interval is calculated. The maximum separation between meat and fat is achieved at the tone-of-grey threshold value which gives the highest variance. The proportion between the number of figures which represents fat and the number of figures for the whole set represents the percentage of the surface which is covered by fat.

The percentage of fat obtained and the thickness af fat determined by means of the probe instrument is used as the basis for the calculation of the class of fatness of the carcass. Included in the calculations used is information of the weight of the carcass and maybe also the shape.

On the basis of the measurements and the calculations it is possible to determine further quality properties of the carcass, such as the muscular volume of certain muscles, which is calculated from the registered weight, contour and thickness of meat.

The computer system 20 may then print out a label on printer 22 which the operator may attach to the carcass before it is again transported by the chain conveyor system of the slaughter line. The label may include information such as carcass identification, data, category, weight, class of fatness, class of conformation, carcass composition and codes for the transportation and treatment control of the individual properties and quality properties of the carcass or parts of this.

Figure 2:
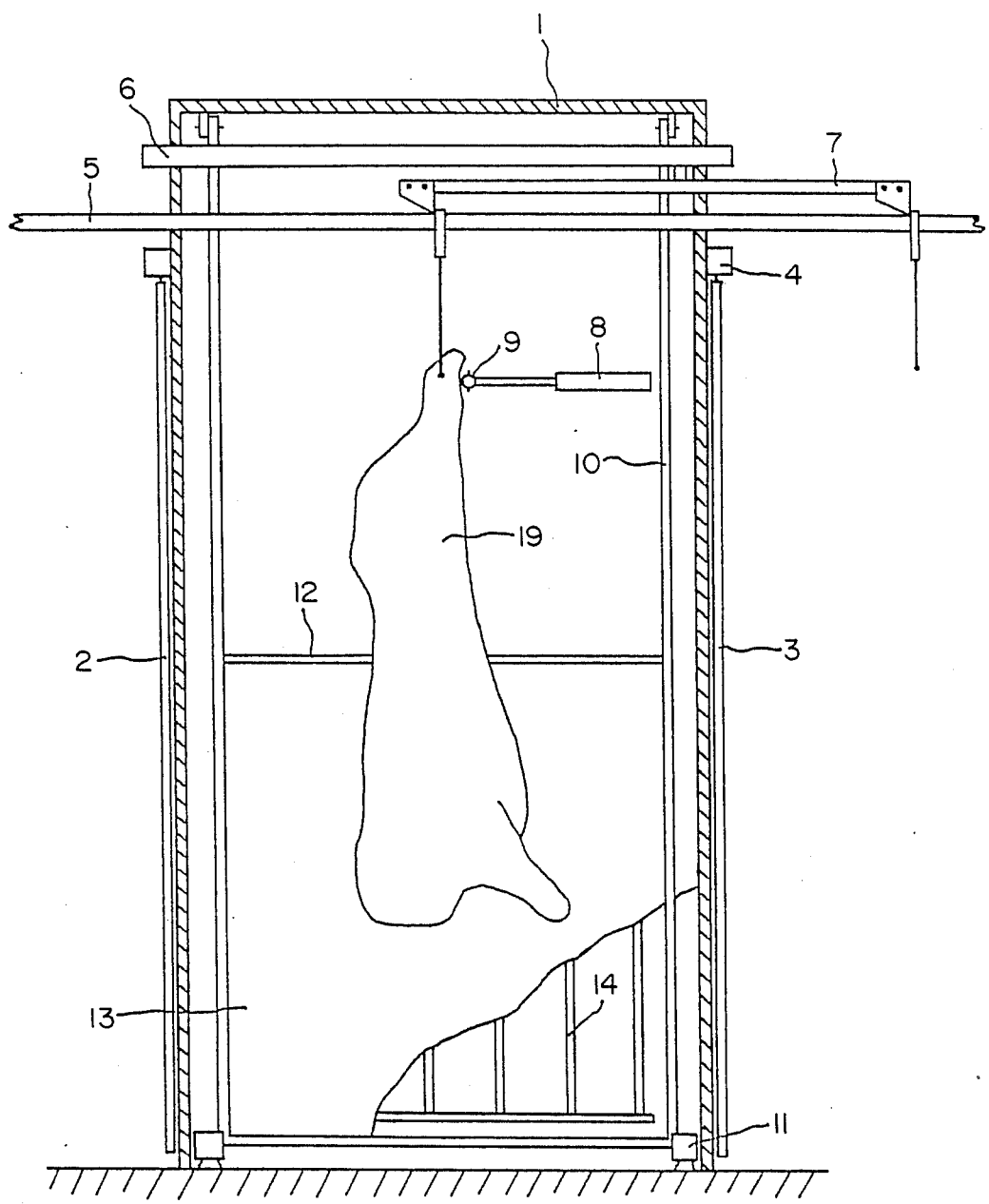
FIG. 2 is a side view of the apparatus of FIG. 1
Figure 3:
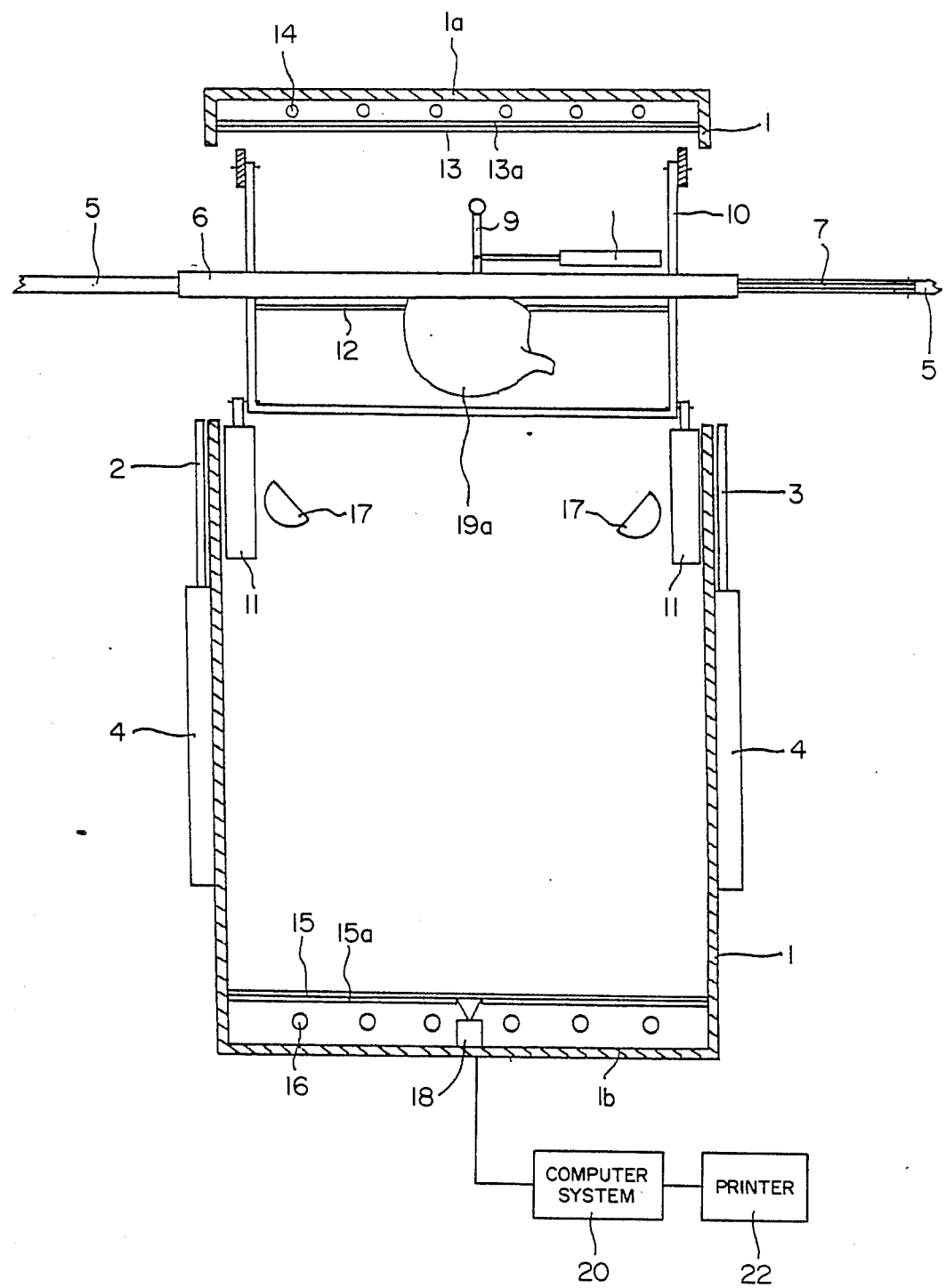
FIG. 3 shows the apparatus of FIG. 1 and FIG. 2 with half of a split carcass.

In FIG. 3 the numbers refer to the same parts as in FIG. 1 and FIG. 2. 19c is half of a split carcass which has been pulled into the chamber and rests on the rod 12 with the outer side facing the camera. The other half of the split carcass is outside the chamber during video recording.

The procedure is the same as the one described above in connection with a whole carcass (FIG. 1 and FIG. 2).

EXAMPLE

In this Example are used 2948 carcasses of a mixed category (unsplit and split young bulls, steers, bulls, unsplit calves, heifers and cows). Trained classifiers perform a subjective classification of the conformation and fatness of the individual carcasses according to the EEC classification system.

Furthermore, objective measurements are carried out on the individual carcasses with the apparatus described above. Two video recordings are made for the determination of the contour of the carcass and the nature of the surface. The probe is inserted at four places into the carcass to determine the thicknesses of meat and fat.

389 carcasses are cut up into saleable meat, fat trim and bone according to a standard procedure and the composition of each carcass is determined.

The provided data are processed in a computer unit by means of a programme system called: "Statistical Analysis System". In this way information is obtained about constants and other criterions of the formulas which are to be used in determining the quality properties of other carcasses.

The formulas are obtained by multiple regression equations. The weight of the individual carcass is used in the formulas. A correction of the level corresponding to the object's category may occur in some of the formulas.

Table 1 shows the factors essential to the formulas.

TABLE 1

|  | Yield of meat (1) | Fat perc. (2) | Muscular Volume (3) | Conformation Cl. (4) | Fatness Class (5) |
|---|---|---|---|---|---|
| Video registration |  |  |  |  |  |
| Weight/carcass length |  |  |  | + | + |
| Weight/area | + |  |  | + |  |
| Area of forequarter/carcass length | + |  | + | + | + |
| Area of hindquarter/Area of forequarter |  |  |  |  |  |
| Slope of thigh | + |  | + | + |  |
| Convexity at thigh/carcass length | + |  | + | + |  |
| Carcass width/length = 0.25 |  |  | + |  |  |
| Carcass width/length = 0.35 |  |  |  |  |  |
| Carcass width/length = 0.45 |  |  |  | (+) |  |
| Probe measurement |  |  |  |  |  |
| Lean thickness, loin | (+) | (+) | (+) | (+) | (+) |
| Fat thickness, loin | (+) | (+) |  |  | (+) |
| Fat thickness, culotte | + | + |  | + | + |
| Level correction at: |  |  |  |  |  |
| Jersey | + | + | + | + |  |
| Splitting | + |  | + | + |  |
| Sex/age | + | + | + |  | + |
| Slaughter weight | + | + | + | + | + |

(1) Percentage of saleable meat (some fat included)
(2) Percentage of fat removed according to the standard cutting procedure
(3) Index determined by the sectional area of the loin and the weight of the hindquarter's cuts (average 100)
(4) Indication of quality class corresponding as close as possible to the EUROP Conformation Class
(5) Indication of quality class corresponding as close as possible to the EUROP Fatness Class After having defined the formulas, the relevant data of each carcass are used in these formulas. The yield of meat, fat percentage, muscular volume, conformation class and fatness class are calculated for each carcass. The values obtained are compared with the corresponding quality properties determined by a classifier or by cutting.

The determinations of the apparatus and the subjective determinations were found to be in good agreement.

|  | Accuracy |
|---|---|
| Conformation Class | 1.01 sub-class step* |
| Fatness Class | 0.57 class step |
| Yield of lean | 1.45% |
| Fat percentage | 1.35% |
| Muscular Volume | 2.92 units |

*(three sub-classes = one class)

Tables 2 and 3 show the number of carcasses of each conformation and fatness Class. The apparatus of this invention is very reliable in classifying the carcasses with mixed shape properties. Between 86 and 91% of these carcasses are classified in the same conformation class or they deviate at the most one sub-class step from the subclass found by subjective determination. Only 2% of the carcasses is classified in classes deviating more than two sub-classes from the conformation class determined by the classifier. The apparatus is also reliable with respect to an objective determination of the fatness class of carcasses, as only 1.5% of the determinations will deviate more than one class step from the subjective determination.

REPEATABILITY

The ability of the apparatus and the classifier to produce the same results by a double measurement is investigated by repeating the measurements on 41 carcasses.

The repeatability accuracy of the apparatus and the classifier are shown in Table 4.

TABLE 4

|  | Yield of meat | Percentage of fat | Muscular Volume | Conformation Class | Fatness Class |
|---|---|---|---|---|---|
| Apparatus of invention |  |  |  |  |  |
| Res. stand. dev. | 0.56% | 0.67% | 2.00 uni. | 0.36 sub-cl. | 0.15 cl. |
| Coeff. of corr. | 0.91 | 0.71 | 0.98 | 0.98 | 0.91 |
| Classifiers |  |  |  |  |  |
| Res. stand. dev. |  |  |  | 0.51 sub-cl. | 0.32 cl. |
| Coeff. of corr. |  |  |  | 0.88 | 0.79 |

The apparatus of the invention shows much better results of the conformation and fatness classes than the ones obtained by the classifier.

The apparatus of the invention may replace a subjective classification and in addition, the results would be more reliable. It will also be much easier to compare the results of the various slaughterhouses.

We claim:

1. A method of classification of a livestock carcass comprising the following steps:

TABLE 2

Class of Conformation
Classification with the apparatus of the invention

| Classifier's evaluation | +4/3 cl. or more | +3/3 cl. | +2/3 cl. | +1/3 cl. | Agreement | −1/3 cl. | −2/3 cl. | −3/3 cl. | −4/3 cl. or more | Numb | % within +/−1/3 Class |
|---|---|---|---|---|---|---|---|---|---|---|---|
| P− | 0 | 1 | 3 | 6 | 47 | — | — | — | — | 57 | (93) |
| P | 0 | 0 | 7 | 18 | 29 | 16 | — | — | — | 70 | (90) |
| P+ | 1 | 1 | 16 | 58 | 61 | 34 | 6 | — | — | 177 | 86 |
| O− | 2 | 8 | 34 | 140 | 174 | 80 | 14 | 1 | — | 453 | 87 |
| O | 5 | 10 | 71 | 229 | 290 | 130 | 17 | 0 | 0 | 752 | 86 |
| O+ | 1 | 4 | 30 | 142 | 272 | 166 | 23 | 0 | 0 | 638 | 91 |
| R− | 0 | 2 | 10 | 77 | 189 | 144 | 35 | 3 | 1 | 461 | 89 |
| R | 0 | 0 | 2 | 26 | 56 | 71 | 26 | 4 | 0 | 185 | 83 |
| R+ | 0 | 2 | 3 | 5 | 22 | 23 | 15 | 5 | 0 | 75 | (67) |
| U− | 0 | 0 | 1 | 3 | 6 | 14 | 10 | 2 | 0 | 36 | (64) |
| U | 0 | 0 | 0 | 1 | 3 | 8 | 11 | 4 | 0 | 27 | (44) |
| U+ | — | 0 | 0 | 0 | 3 | 2 | 2 | 3 | 0 | 10 | (50) |
| E− | — | — | 0 | 0 | 1 | 0 | 4 | 0 | 0 | 5 | (20) |
| E | — | — | — | 0 | 0 | 0 | 1 | 0 | 1 | 2 | (0) |
| E+ | — | — | — | — | 0 | 0 | 0 | 0 | 0 | 0 |  |
| Total | 9 | 28 | 177 | 705 | 1153 | 688 | 164 | 22 | 2 | 2948 |  |
| % | 0 | 1 | 6 | 24 | 39 | 23 | 6 | 1 | 0 | 100 | 86.3 |

TABLE 3

Class of Fatness
Classification with the apparatus of the invention

| Classifier's evaluation | +3 Cl. | +2 Cl. | +1 Cl. | Agreement | −1 Cl. | −2 Cl. | −3 Cl. | Number | % within +/−1 Cl. |
|---|---|---|---|---|---|---|---|---|---|
| Class 1 | 1 | 5 | 128 | 48 | — | — | — | 182 | 97 |
| Class 2 | — | 4 | 256 | 1132 | 97 | — | — | 1489 | 100 |
| Class 3 | — | 10 | 129 | 486 | 401 | 9 | — | 1035 | 98 |
| Class 4 | — | — | 26 | 86 | 80 | 17 | — | 209 | 92 |
| Class 5 | — | — | — | 21 | 10 | 1 | 1 | 33 | 94 |
| Total | 1 | 19 | 539 | 1773 | 588 | 27 | 1 | 2948 |  |
| % | 0 | 1 | 18 | 60 | 20 | 1 | 0 | 100 | 98.5 |

(a) arranging a carcass in a light-screening chamber having opposite first and second outer walls, said first wall constituting a light-emitting surface, said carcass having a first side surface facing said first wall constituting said light-emitting surface and a second side surface facing said second wall, (b) generating a registration of said second side surface of said carcass by means of an electronic camera arranged in said second wall for providing a high contrast registration of said second side surface of said carcass in which high contrast registration said second side surface of said carcass is represented by a totally darkened area in relation to an illuminated background representing said light-emitting surface, (c) determining a contour of said second side surface of said carcass by processing said registration by means of a data processing system, (d) determining a measurement representing a classification of said carcass on the basis of said determination of said contour by means of said data processing system, and (e) outputting said measurement representing said classification of said carcass.

2. A method according to claim 1, wherein in step (d) at least two recognizable points being determined by means of said data processing system from said contour, and wherein in step (d) at least one dimension of said carcass is determined from said points.

3. A method of classification of a livestock carcass comprising the following steps:

(a) arranging a carcass in a light-screening chamber having opposite first and second outer walls, said first wall constituting a light-emitting surface, said carcass having a first side surface facing said first wall constituting said light-emitting surface and a second side surface facing said second wall, (b) generating a registration of said second side surface of said carcass by means of an electronic camera arranged in said second wall for providing a high contrast registration of said second side surface of said carcass, in which high contrast registration, said second side surface of said carcass is represented by a totally darkened area in relation to an illuminated background representing said light-emitting surface, (c) determining a contour of said second side surface of said carcass by processing said registration by means of a data processing system, (d) measuring the thickness of meat and the thickness of fat at respective selected areas of said carcass by inserting a probe into said carcass at said selected areas, (e) determining a measurement representing a classification of said carcass on the basis of said determination of said contour and on the basis of said measurement of said thicknesses of meat and fat at said selected areas of said carcass by means of said data processing system, and (f) outputting said measurement representing said classification of said carcass.

4. A method of classification of a livestock carcass comprising the following steps:

(a) arranging a carcass in a light-screening chamber having opposite first and second outer walls, said first wall constituting a light-emitting surface, said carcass having a first side surface facing said first wall constituting said light-emitting surface and a second side surface facing said second wall, (b) generating a first registration of said second side surface of said carcass by means of an electronic camera arranged in said second wall for providing a high contrast registration of said second side surface of said carcass, in which high contrast registration, said second side surface of said carcass is represented by a totally darkened area in relation to an illuminated background representing said light-emitting surface, (c) determining a contour of said second side surface of said carcass by processing said first registration by means of a data processing system, (d) generating a second registration of said second side surface of said carcass by means of said electronic camera, while said second side surface of said carcass is illuminated by limiting said generation of said second registration to said area determined in step (b) by said first registration of said second side surface of said carcass, for providing a registration indentifying meat and fat areas of said second side surface of said carcass, (e) identifying said meat and fat areas of said second side surface of said carcass from said second registration by means of said data processing system, (f) determining a measurement representing a classification of said carcass on the basis of said determination of said contour and on the basis of said identification of said meat and fat areas of said second side surface of said carcass by means of said data processing system, and (g) outputting said measurement representing said classification of said carcass.

5. A method according to claim 4, wherein in step (d) said second side surface of said carcass is illuminated by diffuse light.

6. A method according to claim 4, wherein said contour determined in step (c) is used in step (d) for defining a partial picture registration of said second side surface in which partial picture registration said meat and fat areas are determined by means of said data processing system.

7. A method according to claim 6, wherein in step (d) at least two points identifying the top point of the curve along the neck of said carcass and the front legs of said carcass are identified, and wherein in step (d) said partial picture is determined by a border line, which intersects said two points.

8. A method of classification of a livestock carcass comprising the following steps:

(a) arranging a carcass in a light-screening chamber having opposite first and second outer walls, said first wall constituting a light-emitting surface, said carcass having a first side surface facing said first wall constituting said light-emitting surface and a second side surface facing said second wall, (b) generating a registration of said second side surface of said carcass by means of an electronic camera arranged in said second wall for providing a high contrast registration of said second side surface of said carcass, in which high contrast registration, said second side surface of said carcass is represented by a totally darkened area in relation to an illuminated background representing said light-emitting surface, (c) determining a contour of said second side surface of said carcass by processing said registration by means of a data processing system, (d) generating a second registration of said second side surface of said carcass by means of said electronic camera, while said second side surface of said carcass is illuminated by limiting said generation of said second registration to said area determined in step (b) by said first registration of said second side surface of said carcass, for providing a registration identifying meat and fat areas of said second side surface of said carcass, (e) identifying said meat and fat areas of said second side surface of said carcass from said second registration by means of said data processing system, (f) measuring the thickness of meat and the thickness of fat at selected areas of said carcass by inserting a probe into said carcass at said selected areas of said carcass, (g) determining a measurement representing a classification of said carcass on the basis of said determination of said contour, on the basis of said identification of said meat and fat areas of said second side surface of said carcass and on the basis of said measurement of the thicknesses of said meat and fat areas of said carcass by means of said data processing system, (h) outputting said measurement representing said classification of said carcass.

9. An apparatus for classification of a livestock carcass, comprising:
(a) a light-screening chamber having opposite first and second outer walls, said first wall constituting a light-emitting surface, and having supporting means for supporting a carcass which is arranged in said light-screening chamber and has a first side surface facing said first wall constituting said light-emitting surface and a second side surface facing said second wall,
(b) an electronic camera arranged in said second wall for generating a high contrast registration of said second side surface of said carcass arranged in said light-screening chamber, in which high-contrast registration, said second side surface of said carcass is represented by a totally darkened area in relation to an illuminated background representing said light-emitting surface,
(c) a data processing system connected to said electronic camera for receiving said high-contrast registration therefrom for processing in said data processing system and for determining a contour of said second side surface of said carcass and further for determining a measure representing a classification of said carcass on the basis of said determination of said contour, and
(d) a data channel for outputting said measure representing said classification of said carcass.

10. An apparatus according to claim 9, said light-emitting surface being a surface of substantially homogenious light-emission intensity.

11. An apparatus for classification of a livestock carcass, comprising:
(a) a light-screening chamber having opposite first and second outer walls, said first wall constituting a light-emitting surface, and having supporting means for supporting a carcass which is arranged in said light-screening chamber and has a first side surface facing said first wall constituting said light-emitting surface and a second side surface facing said second wall,
(b) an electronic camera arranged in said second wall for generating a high contrast registration of said second side surface of said carcass arranged in said light-screening chamber, in which high-contrast registration, said second side surface of said carcass is represented by a totally darkened area in relation to an illuminated background representing said light-emitting surface,
(c) a probe for insertion into said carcass at selected areas, for obtaining measurements representing the thicknesses of meat and fat of said carcass,
(d) a data processing system connected to said electronic camera and to said probe for receiving said high-contrast registration from said electronic camera and said measurements of the thicknesses of meat and fat of said carcass from said probe for processing in said data processing system, for determining a contour of said second side surface of said carcass on the basis of said high-contrast registration, and further for determining a measurement representing a classification of said carcass on the basis of said determination of said contour and on the basis of said measurements representing the thicknesses of meat and fat of said carcass, and
(e) a data channel for outputting said measurement representing said classification of said carcass.

12. An apparatus for classification of a livestock carcass, comprising:
(a) a light-screening chamber having opposite first and second outer walls, said first wall constituting a light-emitting surface, and having supporting means for supporting a carcass which is arranged in said light-screening chamber and has a first side surface facing said wall constituting said light-emitting surface and a second side surface facing said second wall,
(b) an electronic camera arranged in said second wall for generating a first, high contrast registration of said second side surface of said carcass arranged in said light-screening chamber, while said first side surface of said carcass is illuminated by said light-emitting surface, in which first high-contrast registration, said second side surface of said carcass is represented by a totally darkened area in relation to an illuminated background representing said light-emitting surface, and a second registration of said second side surface of said carcass, while said second surface of said carcass is illuminated by means of a light source,
(c) a data processing system connected to said electronic camera for receiving said first and second registrations therefrom for processing in said data processing system, for determining a contour of said second side surface of said carcass on the basis of said first registration, and for identifying meat and fat areas of said second side surface of said carcass on the basis of said second registration, and further for determining a measurement representing a classification of said carcass on the basis of said determination of said contour and on the basis of said identified meat and fat areas of said second side surface of said carcass, and
(d) a data channel for outputting said measure representing said classification of said carcass.

13. An apparatus according to claim 12, wherein said light source for illuminating said second side surface of said carcass generates diffuse light.

14. An apparatus according to claim 13, wherein said light source comprises a frosted, translucent plate, behind which several individual light sources are arranged.

15. An apparatus for classification of a livestock carcass, comprising:
   (a) a light screening chamber having opposite first and second outer walls, said first wall constituting a light-emitting surface, and having supporting means for supporting a carcass which is arranged in said light-screening chamber and has a first side surface facing said first wall constituting said light-emitting surface and a second side surface facing said second wall,
   (b) an electronic camera arranged in said second wall for generating a first, high contrast registration of said second side surface of said carcass arranged in said light-screening chamber, while said first side surface of said carcass is illuminated by said light-emitting surface, in which first high-contrast registration, said second side surface of said carcass is represented by a totally darkened area in relation to an illuminated background representing said light-emitting surface, and a second registration of said second side surface of said carcass, while said second side surface of said carcass is illuminated by means of a light source,
   (c) a probe for insertion into said carcass and for generating measurements representing the thicknesses of meat and fat of said carcass,
   (d) a data processing system connected to said electronic camera and to said probe for receiving said first and second registrations and said measurements representing the thicknesses of meat and fat of said carcass from said electronic camera and said probe, respectively, for processing said first and second registrations and said measurements representing the thicknesses of meat and fat of said carcass in said data processing system, for determining contour of said second side surface of said carcass on the basis of said first registration, for identifying meat and fat areas of said second side surface of said carcass on the basis of said second registration, and further for determining a measurement representing a classification of said carcass on the basis of said determination of said contour, on the basis of said identified meat and fat areas of said second side surface of said carcass and on the basis of said measurements representing the thicknesses of meat and fat of said carcass, and
   (e) a data channel for outputting said measurement representing said classification of said carcass.

* * * * *